United States Patent
Link

(10) Patent No.: US 8,901,362 B2
(45) Date of Patent: Dec. 2, 2014

(54) METHODS AND COMPOSITIONS FOR STYRENE INHIBITION VIA IN SITU GENERATION OF QUINONE METHIDES

(75) Inventor: John Link, Humble, TX (US)

(73) Assignee: General Electric Company, Schenectady, NY (US)

(*) Notice: Subject to any disclaimer, the term of this patent is extended or adjusted under 35 U.S.C. 154(b) by 351 days.

(21) Appl. No.: 13/364,554

(22) Filed: Feb. 2, 2012

(65) Prior Publication Data

US 2013/0204053 A1 Aug. 8, 2013

(51) Int. Cl.
*C07C 7/20* (2006.01)

(52) U.S. Cl.
USPC .................. 585/2; 585/3; 585/4; 585/952

(58) Field of Classification Search
USPC .................................. 585/2, 3, 952
See application file for complete search history.

(56) References Cited

U.S. PATENT DOCUMENTS

| | | | |
|---|---|---|---|
| 3,925,488 A | 12/1975 | Shin | |
| 4,032,547 A | 6/1977 | Bacha et al. | |
| 5,254,760 A | 10/1993 | Winter et al. | |
| 5,470,440 A | 11/1995 | Arhancet | |
| 5,562,863 A | 10/1996 | Arhancet | |
| 5,616,774 A | 4/1997 | Evans et al. | |
| 6,024,894 A | 2/2000 | Arhancet | |
| 6,376,728 B1* | 4/2002 | Eldin et al. | 585/5 |
| 6,388,155 B1 | 5/2002 | Sy et al. | |
| 6,926,820 B2 | 8/2005 | Eldin et al. | |
| 6,960,279 B2* | 11/2005 | Merrill | 203/63 |
| 7,045,647 B2* | 5/2006 | Benage | 560/4 |
| 7,128,826 B2 | 10/2006 | Eldin et al. | |
| 7,473,795 B2* | 1/2009 | Benage | 560/4 |
| 8,128,804 B2* | 3/2012 | Weyler et al. | 208/48 AA |
| 8,298,440 B2* | 10/2012 | Rai et al. | 252/182.29 |
| 2002/0040174 A1 | 4/2002 | Pryce et al. | |
| 2006/0020089 A1* | 1/2006 | Merrill | 526/82 |
| 2006/0163539 A1* | 7/2006 | Nakajima et al. | 252/397 |
| 2010/0168434 A1* | 7/2010 | Loyns et al. | 546/242 |
| 2012/0101295 A1* | 4/2012 | Weyler et al. | 560/2 |

(Continued)

FOREIGN PATENT DOCUMENTS

| | | |
|---|---|---|
| EP | 0737660 A1 | 10/1996 |
| EP | 1604965 A1 | 12/2005 |
| WO | 2011152961 A2 | 12/2011 |

OTHER PUBLICATIONS

Search Report and Written Opinion from corresponding PCT Application No. PCT/US2013/024297 dated May 7, 2013.

(Continued)

*Primary Examiner* — Ellen McAvoy
(74) *Attorney, Agent, or Firm* — Wegman, Hessler & Vanderburg

(57) ABSTRACT

Methods and compositions are provided for inhibiting the polymerization of a vinyl aromatic monomer, such as styrene monomer, during elevated temperature processing or distillation thereof or during storage or shipment of polymer containing product. The compositions include a combination of a hydroxybenzyl alcohol (1) and a dehydration catalyst (2). The combination is added to a vinyl aromatic monomer. Typically, the hydroxybenzyl alcohol is dehydrated in the styrene solution by the use of a strong acid catalyst acting as the dehydration catalyst, and the resultant reaction product is a quinone methide styrene inhibitor.

22 Claims, 2 Drawing Sheets

(56) References Cited

U.S. PATENT DOCUMENTS

| | | | |
|---|---|---|---|
| 2012/0217444 A1* | 8/2012 | Liu et al. | 252/400.53 |
| 2012/0313036 A1* | 12/2012 | Masere | 252/182.29 |
| 2012/0316369 A1* | 12/2012 | Masere | 585/2 |
| 2013/0030225 A1* | 1/2013 | Rai et al. | 585/5 |
| 2013/0072729 A1* | 3/2013 | Link et al. | 585/4 |
| 2013/0116486 A1* | 5/2013 | Loyns et al. | 585/5 |

OTHER PUBLICATIONS

Tummatorn, J., Ruchirawat, S. and Polypradith, P. (2010), A Convergent General Strategy for the Functionalized 2-Aryl Cycloalkyl-Fused Chromans: Intramolecular Hetero-Diels—Alder Reactions of ortho-Quinone Methides . Chem. Eur. J., 16: 1445-1448. doi: 10.1002/chem.200902403.

* cited by examiner

METHODS AND COMPOSITIONS FOR STYRENE INHIBITION VIA IN SITU GENERATION OF QUINONE METHIDES

FIELD OF THE INVENTION

The invention pertains to methods and compositions for inhibiting the undesired polymerization of vinyl aromatic monomers, such as styrene monomers, during processes such as monomer preparation, and purification, and during storage and shipment of products containing such monomers.

BACKGROUND OF THE INVENTION

Common industrial methods for producing styrene typically include separation and purification processes such as distillation to remove unwanted impurities. Unfortunately, purification processes carried out at elevated temperatures result in an increased rate of undesired polymerization. Distillation is generally carried out under vacuum to minimize loss of monomer.

Furthermore, it is well known that styrene monomers readily polymerize when heated. Heat polymerization is rapid. In fact, polymerization increases with increasing temperature. This polymerization is undesirable during many stages of the manufacturing, processing, handling, storage and use of styrene monomers, as it results not only in the loss of desired monomer end-product, but also in the uses of production efficiency caused by polymer formation and/or agglomeration of polymer on process equipment.

To minimize this problem, free radical inhibitors consisting of nitrated phenol-based retarders have been used to inhibit the polymerization. These reagents are typically added prior to the distillation. However, these nitrated phenol-based retarders can be toxic. Thus, there exists a strong need for a green inhibitor that provides an effective means of preventing polymerization.

SUMMARY OF THE INVENTION

In one exemplary embodiment of the invention, a composition is provided for inhibiting the polymerization of a variety of vinyl aromatic monomers. The compositions comprises (1) an hydroxybenzyl alcohol and (2) a dehydration catalyst. In further aspects of the invention, (1) and (2) are present in an amount of 1-99 wt % (1):99-1 wt % (2). In another exemplary embodiment, the weight ratio of (1):(2) is about 2:1 to about 20:1.

The vinyl aromatic monomer may be chosen from a variety of members such as those selected from the group consisting of styrene, bromostyrene, divinyl benzene, α-methylstyrene, and vinyl toluene.

In further exemplary embodiments, the dehydration catalyst is an organic acid and may be chosen from i) alkyl, aryl, and alkaryl sulfonic acids and $C_6$-$C_{22}$ saturated or unsaturated carboxylic acids. In one exemplary embodiment, the organic acid is dodecyl benzene sulfonic acid. In other exemplary embodiments, the hydroxyl benzyl alcohol compound is di-tert butyl hydroxy benzyl alcohol.

In further exemplary embodiments, an hydroxyl amine compound (3) may be conjointly utilized with the hydroxy benzyl alcohol (1) and dehydration catalysts (2). In further exemplary embodiments, a stable free radical, such as a nitroxyl compound, may be conjointly used with the components (1) and (2).

In other aspects of the invention, methods are provided for inhibiting the polymerization of vinyl monomers wherein a quinone methide compound is added to the monomer. In one embodiment, the quinone methide is formed in situ via reaction of a hydroxy benzyl alcohol (1) and a dehydration catalyst (2). In other embodiments of the invention, from about 10-10,000 ppm, collectively, of the components (1) and (2) are added to the vinyl monomer based upon one million parts of the vinyl monomer.

The optional hydroxyl amine compound may be added to the vinyl monomer in an amount of about 1-10,000 ppm hydroxylamine based upon one million parts of the vinyl monomer. Further, in other embodiments, the optional nitroxyl compound may be added to the vinyl monomer in an amount of about 1-10,000 ppm based on one million parts of the vinyl monomer.

The present invention and its advantages over the prior art will become apparent upon reading the following detailed description and the appended claims with reference to the accompanying drawings.

BRIEF DESCRIPTION OF THE DRAWINGS

These and other aspects of the invention will be understood from the description and claims herein, taken together with the drawings showing details of construction and illustrative embodiments, wherein:

DETAILED DESCRIPTION OF EXEMPLARY EMBODIMENTS

Figure 1:
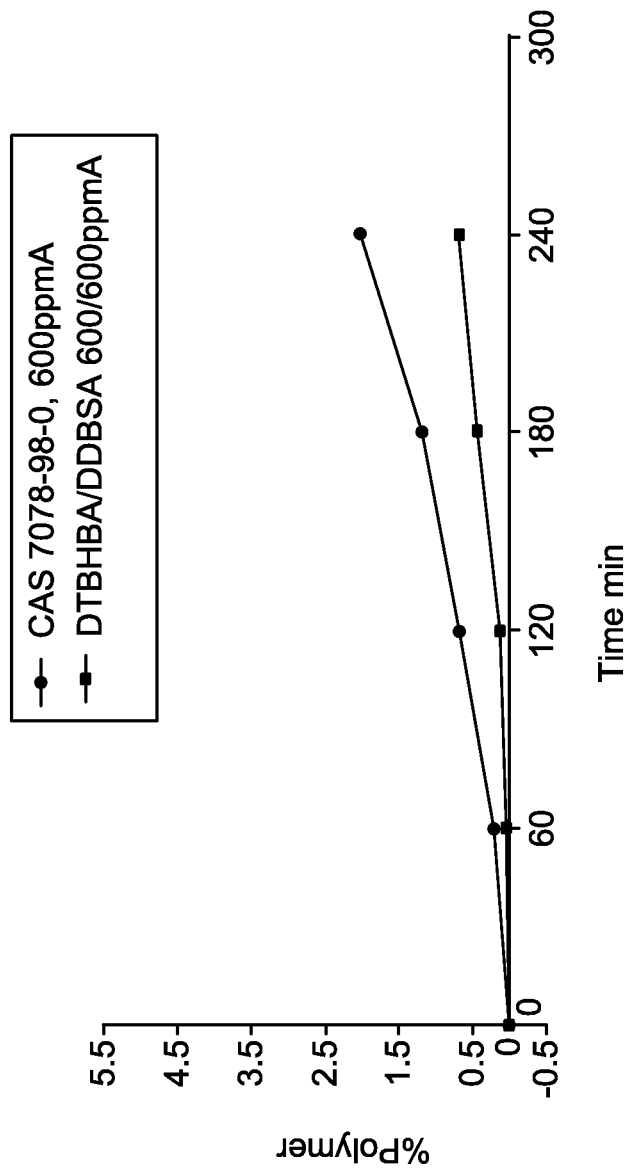
FIG. 1 is a graph depicting the percentage of polymer produced when di-tertbutyl hydroxybenzyl alcohol (i.e., DTBHBA) plus dodecylbenzenesulfonic acid (i.e., DDBSA) is added to the styrene solution and when a quinone methide is added to the styrene solution in the present invention.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges stated herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

As used herein, the terms "comprises", "comprising", "includes", "including", "has", "having", or any other variation thereof, are intended to cover a non-exclusive inclusion. For example, a process, method, article or apparatus that comprises a list of elements is not necessarily limited to only those elements, but may include other elements not expressly listed or inherent to such process, method, article, or apparatus.

The singular forms "a", "an", and "the" include plural referents unless the context clearly dictates otherwise.

In accordance with one aspect of the invention, a quinone methide polymerization inhibitor is added to the vinyl monomer. Although applicant is not bound to any particular theory of operation, the quinone methide is in situ generated by the dehydrating action of a strong acid catalyst on a hydroxylbenzyl alcohol. As to the hydroxybenzyl alcohols (1) that may be used, these may generally be of the type given in Formula I:

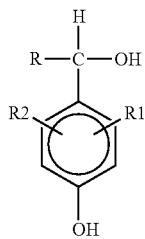
(I)

wherein R is H, or $C_1$-$C_{10}$ alkyl, or $C_6$-$C_{20}$ alkylaryl, $R_1$ and $R_2$ may or may not be present and are independently selected from $C_1$-$C_{10}$ alkyl groups, preferably $C_1$-$C_6$ alkyl groups. At present, the preferred hydroxybenzyl alcohol is 3,5-di-tertbutyl 4-hydroxybenzyl alcohol (i.e., di-tertbutyl hydroxylbenzyl alcohol).

The dehydrating catalyst (2) is a strong acid catalyst and, in certain exemplary embodiments, may be chosen from alkyl, aryl, and alkylaryl sulfonic acids (the number of C atoms being between about 1-40), and $C_2$-$C_{36}$ saturated or unsaturated carboxylic acids. For example, alkyl benzene sulfonic acids such as dodecylbenzene sulfonic acid and toluene sulfonic acid such as para toluene sulfonic acid may be mentioned as exemplary. Further, stearic acid is an example of a $C_2$-$C_{36}$ saturated carboxylic acid that may be mentioned.

In accordance with one exemplary embodiment, an hydroxylamine inhibitor can be conjointly used with (1) and (2) above. Hydroxylamines have the functional groups —NOH— and may be represented by the general Formula II:

(II)

wherein $R_3$ and $R_4$ may be the same or different and are selected from hydrogen, alkyl, aryl, alkaryl, or hydroxyalkyl groups and preferably have about three to about 20 carbon atoms. In one exemplary embodiment, the hydroxylamine is 2-propanol, 1,1'-(hydroxyimino)bis. Details pertaining to the hydroxylamines can be seen in U.S. Pat. No. 6,024,894 (Arhancet)—incorporated herein by reference.

In still other embodiments, the hydroxybenzyl alcohol (1) and dehydrating catalyst (2) may be employed as a polymerization inhibitor conjointly with a stable free radical, such as the nitroxyl compounds. Exemplary nitroxyl compounds that may be mentioned are 4-hydroxy-2,2,6,6-tetramethyl-1-piperidinyloxy, or tetramethylpiperidino-N-oxyl, or 1-oxyl-2,2,6,6-tetramethyl-4-piperidinol. Details about the nitroxyl free radicals can be seen for example in U.S. Pat. No. 5,254,760 (Winter et al.)—incorporated by reference herein.

The compositions and methods of the present invention are effective at inhibiting polymerization of vinyl aromatic monomers under processing and storage conditions. Exemplary processing conditions include but are not limited to preparation, purification, distillation and vacuum distillation processes.

Styrene, for example, is typically processed at temperatures between 75° C. and 125° C. In one aspect of the invention, the compositions and methods of the present invention are effective at inhibiting the polymerization of styrene over this range of temperatures.

The vinyl aromatic monomers that are treated by the compositions and methods of the present invention include but are not limited to styrene, bromostyrene, divinylbenzene, and α-methylstyrene. The compositions and methods of the present invention are particularly efficacious at inhibiting the polymerization of styrene monomer.

The total amount of hydroxybenzyl alcohol (1) and dehydration catalyst (2) used in the methods of the present invention is that amount which is sufficient to inhibit polymerization of vinyl aromatic monomers. This amount will vary according to the conditions under which the vinyl aromatic monomer is being processed, contaminants in the system and the temperature of the system. At higher processing temperatures and higher monomer contamination, larger amounts of the inhibiting composition are required.

For purposes of the present invention, the term "effective inhibiting amount" is that amount which is effective at inhibiting vinyl aromatic monomer polymerization. In one embodiment, this amount ranges from about 1 part to about 10,000 parts of hydroxybenzyl alcohol (1) and dehydration catalyst, collectively, per 1 million parts of monomer. In another embodiment, this amount will range from about 1 to about 1,500 parts per million parts monomer.

Accordingly, it is possible to produce a more effective vinyl aromatic monomer polymerization inhibiting treatment than is obtained by the use of either compound by itself when measured at comparable treatment levels. This synergism or enhanced activity between components allows for the concentration of each of the components to be lowered and the total quantity of polymerization inhibitor required, particularly at higher temperatures, may be lowered while achieving a commensurate level of polymerization inhibition.

As such, one exemplary weight ratio of hydroxybenzyl alcohol (1) to dehydration catalyst (2) will generally range from about 2:1 to about 4:1. In one embodiment, the weight ratio is about 2:1 to about 20:1.

The compositions of the present invention can be introduced into the vinyl aromatic monomer by any conventional method at any point of the processing system, either as separate and individual ingredients or as a combination of ingredients.

The compositions of the present invention may be added to the vinyl aromatic monomer as either a dispersion or as a solution using a suitable liquid carrier or solvent. Any solvent that is compatible with the individual ingredients of the composition and the vinyl aromatic monomer to be treated may be employed. It is often desirable to dissolve the inhibitors in the monomer to which the inhibitor is being added to avoid introducing additional impurities in the monomer. Exemplary liquid carriers include organic solvents, such as ethyl benzene, water, glycols, and glycol ethers.

The method of the present invention can control the fouling of processing equipment, such as the equipment used in separation and purification processes of styrene monomer, which is due to or caused by the polymerization of the monomer. The instant invention may be used as both a process inhibitor, which is employed during preparation and processing (e.g., employing heat) of the styrene monomer, and as a product inhibitor, which is combined with the styrene monomer in order to inhibit polymerization during storage and handling.

The invention will now be described in conjunction with the following examples which should be viewed as being illustrative of the invention and should not be deemed to limit the invention in any manner.

EXAMPLES

The effect of a combined treatment of di-tertiary butyl hydroxybenzyl alcohol (DTBHBA) and dodecylbenzene sulfonic acid (DDBSA) on the thermal polymerization of styrene at 120° C. was evaluated by comparing polymer formation utilizing the following procedure.

Uninhibited styrene (5 mL) was placed in a test tube and the appropriate amount of polymerization inhibitor(s) was added, either a known inhibitor compound 4-benzylidene-2, 6-ditert-butyl-2,5 cyclohexadien-1-one (CAS 7078-98-0) as a comparative inhibitor, or the claimed inhibitor composition [DTBHBA/DDBSA]. The tube was capped with a rubber septum and argon was bubbled through the liquid at 10 mL/min. for 3 minutes. The tubes were then placed in an oil bath heated to 120° C. Once the temperature reached 120° C., the stop clock was started and this time was considered as time zero. About 5 ml of the sample was removed from the test tube at varying time intervals for up to 4 hours and measured precisely before pouring into about 40 ml methanol to precipitate out the styrene polymer. The precipitated polystyrene was filtered with a gas membrane filter, dried at 100° C. and weighed. The results of this testing are presented in Table I.

TABLE I

Styrene Polymerization Results

| Time in Minutes | CAS 7078-98-0 600 ppmA | DTBHBA 600 ppmA | DTBHBA/DDBSA 600/600 ppmA | DDBSA 600 ppmA |
|---|---|---|---|---|
| Mg 2.5 mL | | | | |
| 0 | 0 | 0 | 0 | 0 |
| 60 | 4.7 | 193.4 | 0.8 | 53 |
| 120 | 15.6 | | 3.2 | 109.2 |
| 180 | 27.2 | | 10.1 | |
| 240 | 46.1 | | 15.8 | |
| (%) Polymer | | | | |
| 0 | 0 | 0 | 0 | 0 |
| 60 | 0.21 | 8.50 | 0.04 | 2.33 |
| 120 | 0.69 | | 0.14 | 4.80 |
| 180 | 1.20 | | 0.44 | |
| 240 | 2.03 | | 0.69 | | ppmA = ppm actives basis

The results presented in Table I demonstrate that the invention composition is more effective than either ingredient by itself. (See FIG. 1).

Uninhibited styrene (5 mL) was placed in a test tube and varying ratios of DTBHBA/DDBSA were added. The tube was capped with a rubber septum and argon was bubbled through the liquid at 10 mL/min. for 3 minutes. The tubes were then placed in an oil bath heated to 120° C. Once the temperature reached 120° C., the stop clock was started and this time was considered as time zero. About 5 ml of the sample was removed from the test tube at varying time intervals for up to 4 hours and measured precisely before pouring into about 40 ml methanol to precipitate out the styrene polymer. The precipitated polystyrene was filtered with a gas membrane filter, dried at 100° C. and weighed. The results of this testing are presented in Table II.

TABLE II

Styrene Polymerization Results at 120° C. with different ratios of DTBHBA/DDBSA.

| Time in Minutes | DTBHBA/DDBSA 600/600 ppmA | DTBHBA/DDBSA 600/300 ppmA | DTBHBA/DDBSA 600/150 ppmA | DTBHBA/DDBSA 600/50 ppmA | DTBHBA/DDBSA 600/25 ppmA |
|---|---|---|---|---|---|
| Mg 2.5 mL | | | | | |
| 0 | 0 | 0 | 0 | 0 | 0 |
| 60 | 1.2 | 1 | 0.6 | 1.5 | 1.8 |
| 120 | 4.1 | 3.2 | 4.2 | 4.4 | 8.1 |
| 180 | 8.9 | 6.5 | 12.3 | 20.4 | 36.1 |
| 240 | 16.2 | 10.1 | 24.9 | 59.2 | 124.2 |
| (%) Polymer | | | | | |
| 0 | 0 | 0 | 0 | 0 | 0 |
| 60 | 0.05 | 0.04 | 0.03 | 0.07 | 0.08 |
| 120 | 0.18 | 0.14 | 0.18 | 0.19 | 0.36 |
| 180 | 0.39 | 0.29 | 0.54 | 0.90 | 1.59 |
| 240 | 0.71 | 0.44 | 1.09 | 2.60 | 5.46 |

Figure 2:
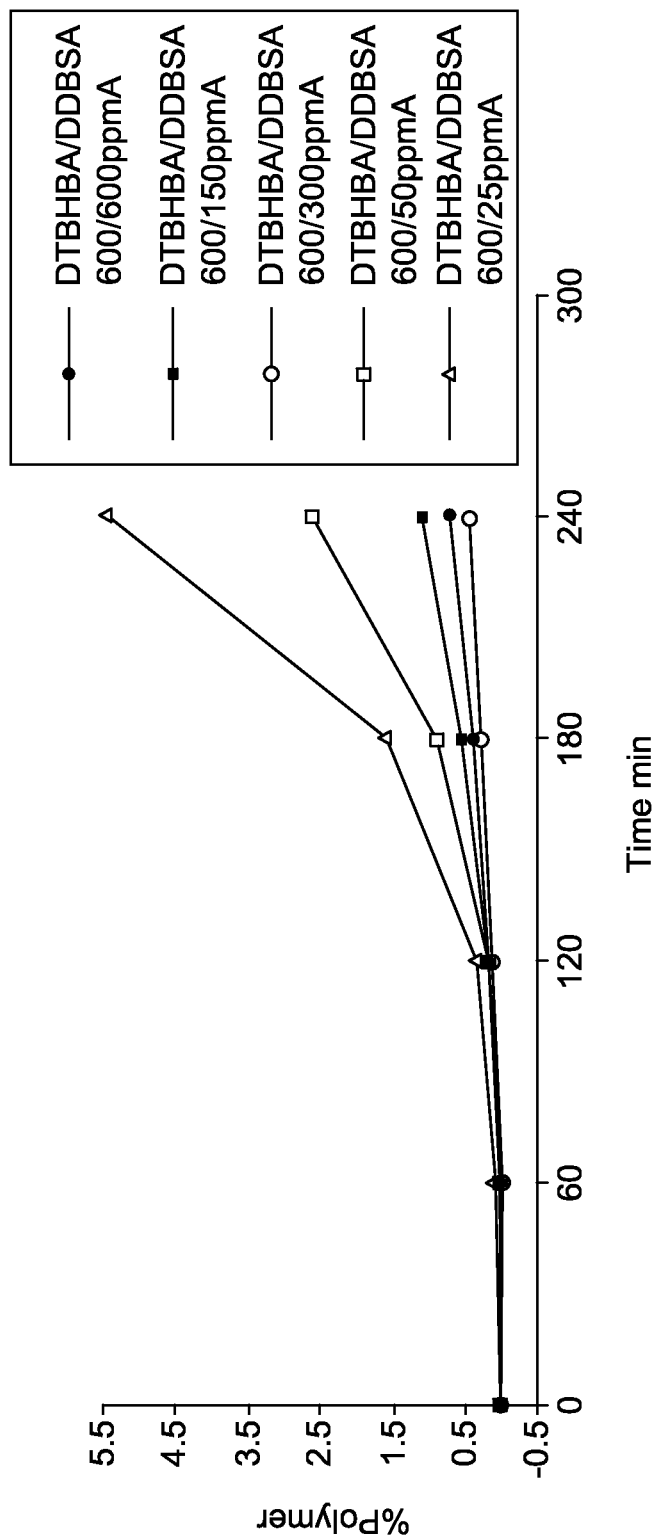
FIG. 2 is a graph depicting multiple ratios of DTBHBA plus DDBSA and the resultant percentage of polymer that is produced in the present invention.

The results presented in Table II demonstrate that the invention composition is more effective at a DTBHBA/DDBSA 600/300 ppm ratio, than at the other ratios. (See FIG. 2).

While this invention has been described in conjunction with the specific embodiments described above, it is evident that many alternatives, combinations, modifications and variations are apparent to those skilled in the art. Accordingly, the preferred embodiments of this invention, as set forth above are intended to be illustrative only, and not in a limiting sense. Various changes can be made without departing from the spirit and scope of this invention. Therefore, the technical scope of the present invention encompasses not only those embodiments described above, but also all that fall within the scope of the appended claims.

What is claimed is:

1. A composition for inhibiting the polymerization of a vinyl aromatic monomer comprising:
   (1) a hydroxybenzyl alcohol; and
   (2) a dehydrating catalyst.

2. A composition as recited in claim 1 wherein said (1) and (2) are present in an amount of about 1-99 wt % (1) 99-1 wt % (2).

3. A composition as recited in claim 2, wherein the weight ratio of (1):(2) is about 2:1 to about 20:1.

4. A composition as recited in claim 1, wherein said vinyl aromatic monomer is a member selected from the group consisting of styrene, bromostyrene, divinylbenzene, and α-methylstyrene.

5. A composition as recited in claim 1 wherein said dehydrating catalyst (2) is an acid chosen from i) alkyl, aryl, and alkylaryl sulfonic acids and ii) $C_2$-$C_{36}$ saturated or unsaturated carboxylic acids.

6. A composition as recited in claim 5 wherein said dehydrating catalyst is an alkyl, aryl, or alkylaryl sulfonic acid.

7. A composition as recited in claim 1, wherein said hydroxylbenzyl alcohol is di-tert butyl hydroxybenzyl alcohol.

8. A composition as recited in claim 1 wherein said dehydrating catalyst is dodecyl benzene sulfonic acid or para toluene sulfonic acid.

9. A composition as recited in claim 1 further comprising a 3) hydroxylamine compound wherein said hydroxylamine is present in an amount of 1-99 wt % based on the total weight of (1) and (2).

10. A composition as recited in claim 1 further comprising (4) a nitroxyl compound, said 4) being present in an amount of 1-99 wt % based on the total weight of (1) and (2).

11. A method for inhibiting the polymerization of a vinyl monomer comprising adding to said monomer (1) a hydroxybenzyl alcohol and (2) a dehydrating catalyst.

12. A method as recited in claim 11 wherein said (1) and (2) are present in an amount of about 1-99 wt % (1):99-1 wt % (2).

13. A method as recited in claim 11 wherein the weight ratio of (1):(2) is about 2:1 to about 20:1 and wherein about 10-10,000 ppm of said (1) and (2) combined is added to said vinyl monomer, based upon one million parts of said vinyl monomer.

14. A method as recited in claim 11 wherein said dehydrating catalyst is an acid chosen from i) alkyl, aryl, and alkylaryl sulfonic acids and ii) $C_6$-$C_{22}$ saturated or unsecured carboxylic acids.

15. A method as recited in claim 11 wherein said hydroxylbenzyl alcohol is di-tert butyl hydroxylbenzyl alcohol.

16. A method as recited in claim 14 wherein said acid is dodecyl benzene sulfonic acid or para toluene sulfonic acid.

17. A method as recited in claim 11 further comprising adding to said vinyl monomer a (3) hydroxylamine compound, said hydroxylamine being added in an amount of about 1-10,000 ppm hydroxylamine based on 1 million parts of said vinyl monomer.

18. A method as recited in claim 11 further comprising adding to said vinyl monomer a (4) nitroxyl compound, said nitroxyl compound being added in an amount of about 1-10,000 ppm based on 1 million parts of said vinyl monomer.

19. A method for inhibiting the polymerization of a vinyl monomer comprising adding to said vinyl monomer an effective amount of the composition of claim 1.

20. A method as recited in claim 19 wherein said composition comprises di-tertbutyl hydroxybenzyl alcohol and dodecyl benzene sulfonic acid or para toluene sulfonic acid.

21. A composition as recited in claim 1 wherein said hydroxylbenzyl alcohol has the formula

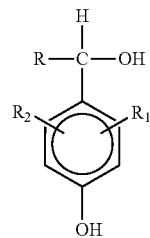

wherein R is H, or $C_1$-$C_{10}$ alkyl, or $C_6$-$C_{20}$ alkylaryl, $R_1$ and $R_2$ may or may not be present and are independently selected from $C_1$-$C_{10}$ alkyl groups.

22. A method as recited in claim 11 wherein said hydroxylbenzyl alcohol has the formula

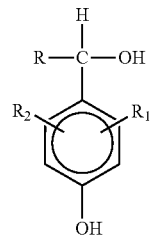

wherein R is H, or $C_1$-$C_{10}$ alkyl, or $C_6$-$C_{20}$ alkylaryl, $R_1$ and $R_2$ may or may not be present and are independently selected from $C_1$-$C_{10}$ alkyl groups.

* * * * *

UNITED STATES PATENT AND TRADEMARK OFFICE
CERTIFICATE OF CORRECTION

| | | |
|---|---|---|
| PATENT NO. | : 8,901,362 B2 | Page 1 of 1 |
| APPLICATION NO. | : 13/364554 | |
| DATED | : December 2, 2014 | |
| INVENTOR(S) | : John Link | |

It is certified that error appears in the above-identified patent and that said Letters Patent is hereby corrected as shown below:

In the Claims

In Claim 2, column 6, lines 43 through 45, it should read as follows:

2. A composition as recited in claim 1 wherein said (1) and (2) are present in an amount of about 1-99 wt% (1) : 99-1 wt% (2).

Signed and Sealed this
First Day of March, 2016

Michelle K. Lee
*Director of the United States Patent and Trademark Office*